(12) United States Patent
Jang et al.

(10) Patent No.: US 10,369,087 B2
(45) Date of Patent: Aug. 6, 2019

(54) RAPID-SETTING HYDRAULIC BINDER COMPOSITION

(71) Applicant: Maruchi, Wonju-si (KR)

(72) Inventors: Sung Wook Jang, Seoul (KR); Kye Hong Cho, Seoul (KR); Jin Sang Cho, Jecheon-si (KR); Moon Kwan Choi, Danyang-gun (KR); Ki Yeon Moon, Chungju-si (KR)

(73) Assignee: MARUCHI, Wonju-si, Gangwon-Do (KR)

( * ) Notice: Subject to any disclaimer, the term of this patent is extended or adjusted under 35 U.S.C. 154(b) by 282 days.

(21) Appl. No.: 15/460,728

(22) Filed: Mar. 16, 2017

(65) Prior Publication Data

US 2017/0181931 A1 Jun. 29, 2017

Related U.S. Application Data

(63) Continuation of application No. PCT/KR2015/009675, filed on Sep. 15, 2015.

(30) Foreign Application Priority Data

Sep. 16, 2014 (KR) .................. 10-2014-0122694

(51) Int. Cl.
| | |
|---|---|
| *C04B 7/02* | (2006.01) |
| *C04B 7/13* | (2006.01) |
| *C04B 11/30* | (2006.01) |
| *C04B 22/10* | (2006.01) |
| *C04B 28/06* | (2006.01) |
| *C04B 103/14* | (2006.01) |
| *C04B 111/00* | (2006.01) |
| *A61K 6/06* | (2006.01) |
| *A61K 6/02* | (2006.01) |
| *A61K 6/04* | (2006.01) |
| *A61K 6/00* | (2006.01) |

(52) U.S. Cl.
CPC .......... *A61K 6/0606* (2013.01); *A61K 6/0008* (2013.01); *A61K 6/02* (2013.01); *A61K 6/04* (2013.01); *A61K 6/0618* (2013.01); *A61K 6/0625* (2013.01); *A61K 6/0631* (2013.01); *A61K 6/0668* (2013.01); *A61K 6/0675* (2013.01); *C04B 7/02* (2013.01); *C04B 7/13* (2013.01); *C04B 11/30* (2013.01); *C04B 22/103* (2013.01); *C04B 28/06* (2013.01); *C04B 2103/14* (2013.01); *C04B 2111/00836* (2013.01)

(58) Field of Classification Search
CPC .......... A61K 6/0606; A61K 6/02; A61K 6/04; A61K 6/0008; A61K 6/0618; A61K 6/0625; A61K 6/0631; A61K 6/0668; A61K 6/0675; C04B 7/02; C04B 7/13; C04B 11/30; C04B 22/103; C04B 28/06; C04B 2103/14; C04B 2111/00836

See application file for complete search history.

(56) References Cited

U.S. PATENT DOCUMENTS

| | | | | |
|---|---|---|---|---|
| 5,273,579 | A * | 12/1993 | Tanaka .................. | C04B 7/21 106/715 |
| 5,366,549 | A * | 11/1994 | Imaizumi .............. | C04B 28/065 106/695 |
| 5,415,547 | A | 5/1995 | Torabinejad et al. | |
| 5,560,774 | A * | 10/1996 | Burge .................... | C04B 28/02 106/692 |
| 7,445,668 | B2 * | 11/2008 | Sommain ............... | C04B 7/345 106/693 |
| 8,974,586 | B2 | 3/2015 | Richard et al. | |
| 2004/0117030 | A1 * | 6/2004 | Axen ..................... | A61L 27/10 623/23.51 |
| 2005/0263036 | A1 | 12/2005 | Primus | |
| 2006/0102053 | A1 | 5/2006 | Engqvist et al. | |
| 2006/0167148 | A1 | 7/2006 | Engqvist et al. | |
| 2007/0009858 | A1 | 1/2007 | Hatton et al. | |
| 2010/0072294 | A1 * | 3/2010 | Nakashima ............ | C04B 28/02 239/1 |
| 2010/0143488 | A1 | 6/2010 | Oguro | |
| 2013/0025498 | A1 | 1/2013 | Richard et al. | |
| 2014/0371351 | A1 * | 12/2014 | Dantin ................... | C04B 28/02 524/5 |
| 2015/0047531 | A1 | 2/2015 | Jang | |

FOREIGN PATENT DOCUMENTS

| | | | | |
|---|---|---|---|---|
| CN | 102649629 | A * | 8/2012 | |
| CN | 104003631 | A * | 8/2014 | |
| JP | 2000264709 | A * | 9/2000 | .............. C04B 2/04 |
| JP | 2006502106 | A | 1/2006 | |
| KR | 20090098783 | A | 9/2009 | |
| KR | 101220535 | B1 | 1/2013 | |
| KR | 20130041804 | A | 4/2013 | |
| KR | 101359073 | B1 | 2/2014 | |
| RU | 2552277 | C1 * | 6/2015 | |
| RU | 2566159 | C1 * | 10/2015 | |

* cited by examiner

*Primary Examiner* — Anthony J Green
(74) *Attorney, Agent, or Firm* — Dinsmore & Shohl LLP; Yongsok Choi, Esq.

(57) ABSTRACT

The present invention relates to a rapid-setting hydraulic binder composition and, more specifically, to a hydraulic binder composition, which contains tricalcium aluminate (C3A) and dodecacalcium heptaaluminate (C12A7), and thus is rapidly set, has an easily adjustable setting time, and is bio-friendly.

10 Claims, 2 Drawing Sheets

RAPID-SETTING HYDRAULIC BINDER COMPOSITION

CROSS-REFERENCE TO RELATED APPLICATIONS

This application is a continuation application of Patent Cooperation Treaty (PCT) international application Serial No. PCT/KR2015/009675, filed on Sep. 15, 2015, and which designates the United States, which claims priority to Korean Patent Application Serial No. 10-2014-0122694, filed on Sep. 16, 2014. The entire contents of PCT international application Serial No. PCT/KR2015/009675, and Korean Patent Application Serial No. 10-2014-0122694 are hereby incorporated by reference.

FIELD OF THE INVENTION

The present invention relates to a rapid-setting hydraulic binder composition, and more specifically, to a biocompatible hydraulic binder composition comprising tricalcium aluminate (C3A) and dodecacalcium heptaaluminate (C12A7) and having very short and easily adjustable hardening time. The present invention is useful for medical use, particularly for dental use.

BACKGROUND

Hydraulic binders with short hardening time, such as dental MTA (Mineral Trioxide Aggregate) or industrial shotcrete may be useful depending on the fields. Among these, dental MTA has been introduced by Torabinejad et al. in the form of a mixture of Portland cement and a radiopaque material. In connection with the constitution of the MTA, reference can be made to US 2005/0263036 and U.S. Pat. No. 5,415,547 (the contents of which are incorporated herein in their entirety).

MTA is mainly used for root canal filling, pulp capping, and restoration of root perforation sites, for example. Portland cement, which is the main component of the MTA, includes tricalcium silicate (C3S), dicalcium silicate (C2S), tricalcium aluminate, tetracalcium aluminoferrite (C4AF) and the like. In the case of the MTA, calcium sulphate may be added to suppress the rapid hydration reaction of calcium aluminate in early stages.

Since the MTA acts on sites where body fluids, saliva and other liquids are present, it should be hardened stably and quickly to have hermeticity. However, unfortunately, the MTA made of conventional Portland cement has a long hardening time of about three hours, which results in insufficient washing resistance and poor workability.

Therefore, there has been introduced the MTA in which calcium chloride is added to Portland cement to reduce the hardening time to about 57 minutes. In connection with this, reference can be made to US 2007/0009858 (the contents of which are incorporated herein in their entirety). However, the above hardening time is also still long in clinical aspects. Particularly, in the case of tooth reimplantation whose procedure time should be shortened to 11 minutes or less, rapid hardening of the MTA becomes more important. Further, even in the case of daily dental pulp treatment such as direct pulp capping, a short hardening time of 10 minutes or less is desired because it is required to reduce the number of procedures so that the number of hospital visits can be reduced and the convenience in performing the procedures can be maximized.

Accordingly, the use of calcium aluminate can be considered. It is known that the addition of calcium aluminate at 40 to 60% of the weight of Portland cement can reduce the hardening time to about 15 minutes. In connection with this, reference can be made to US 2005/0263036 (the contents of which are incorporated herein in their entirety). However, when a large amount of calcium aluminate is added as above, the amount of calcium hydroxide produced from the MTA is reduced to hinder antibacterial effects and tissue regeneration effects caused by the calcium hydroxide.

Therefore, there is a need for a novel rapid-setting hydraulic binder composition that can achieve a short hardening time, hardening time control performance, hermeticity, antibacterial property and biocompatibility, without excessive addition of calcium aluminate.

SUMMARY

One object of the present invention is to solve all the above-described problems in the prior art.

Another object of the invention is to provide a biocompatible hydraulic binder composition that can be hardened within 10 minutes to enhance medical or dental usability, can effectively suppress the infiltration of body fluids or saliva during the use thereof, and can facilitate regeneration of body tissue components such as tertiary dentin, lamina dura, and hydroxyapatite.

According to one aspect of the invention to achieve the above objects, there is provided a rapid-setting hydraulic binder composition, comprising tricalcium aluminate (C3A), dodecacalcium heptaaluminate (C12A7), and calcium hydroxide.

According to another aspect of the invention, there is provided a rapid-setting hydraulic binder composition, comprising Portland cement calcined at a low temperature of 800° C. to 1,250° C., wherein the Portland cement comprises tricalcium aluminate (C3A) and dodecacalcium heptaaluminate (C12A7).

In addition, there are further provided other compositions to implement the invention.

According to the invention, there is provided a biocompatible rapid-setting hydraulic binder composition that can be hardened within 10 minutes.

DETAILED DESCRIPTION

Figure 1:
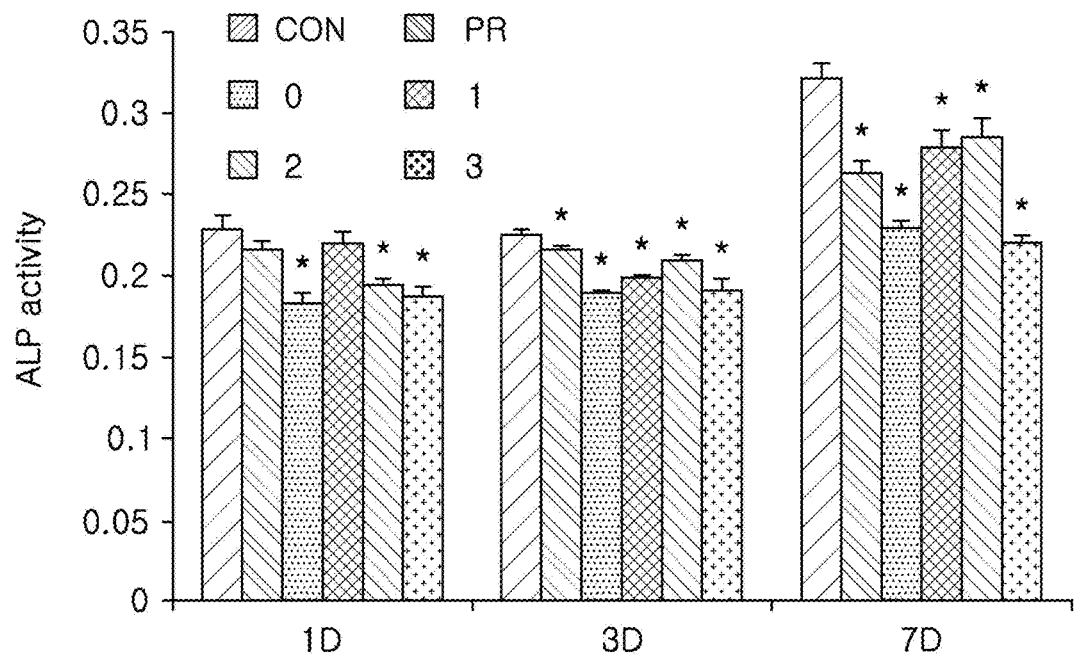
FIG. 1 is a graph obtained from a test conducted according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the locations or arrangements of individual elements within each of the embodiments may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

The basic methods for preparing a biocompatible rapid-setting hydraulic binder composition according to embodiments of the invention may be as follows:

Preparation Method I

C3A is commonly contained in common (white) Portland cement. The composition of the invention may be prepared by adding C12A7 (possibly pulverized) to Portland cement (possibly pulverized) and, if necessary, adding calcium hydroxide (possibly pulverized).

Preparation Method II

It is already known that Portland cement can be produced by calcining and processing clinker for cement production. However, according to this preparation method, the clinker for cement production can be calcined below a temperature at which it is all converted to C3A, so that both C3A and C12A7 are present in some amounts in the resulting Portland cement. That is, the calcination is performed at a temperature of 800 to 1,250° C., whereas the temperature of complete calcination for common Portland cement is 1,450° C., so that C3A and C12A7 coexist in the produced Portland cement. If necessary, calcium hydroxide (possibly pulverized) can be added to the above composition (possibly pulverized) to prepare the composition of the invention.

Hereinafter, various components that can be basically or selectively contained in the composition of the invention as prepared by the above methods will be described in detail.

C3A and C12A7

Calcium aluminate is a continuous solid solution of calcium oxide (CaO) and alumina ($Al_2O_3$) and has various mineral properties depending on the composition ratio. Usually, calcium oxide and alumina are denoted as C and A (which are mostly applied in the following description). C3A and other calcium aluminates (CA, CA2, C12A7, etc.) present in Portland cement can produce hydration minerals such as ettringite ($3CaO.Al_2O_3.3CaSO_4.32H_2O$) to exhibit toughness.

Specifically, calcium aluminate reacts violently with a gypsum component eluted from water or Portland cement to produce needle-like ettringite crystals. The ettringite crystals bind particles of cement or aggregates to exhibit rapid-setting properties.

For example, C3A ($3CaO.Al_2O_3$) can produce ettringite through the reaction of the following equation:

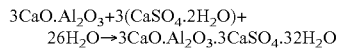

For another example, in the case of C12A7 ($12CaO.7Al_2O_3$), the reaction equation for producing ettringite may be as follows:

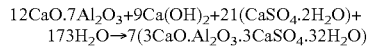

Here, when the gypsum component is insufficient, mono-sulfate hydrate ($3CaO.Al_2O_3.CaSO_4.12H_2O$) having a relatively short crystalline form can be produced.

The hydration of C3A and C12A7 as described above is important for the development of strength (particularly initial strength) of a hardened body produced from the composition of the invention.

Meanwhile, the aforementioned ettringite is a hydrate containing 32 moles of water per molecule, advantageously allowing the water surrounding the composition of the invention to be rapidly fixed and gelled, and forming cross-linkage with needle-like crystals without coating the particles of Portland cement, so that the subsequent hydration reaction of the Portland cement particles is not hindered.

Further, since the ettringite has a structure comparable to a steel frame of a building, a more dense hardened body can be formed while alite (C3S) that can be contained in the composition of the invention becomes calcium silicate hydrate (C—S—H) over time to fill the pores in the ettringite. Meanwhile, the hardened body is water-resistant so that it does not dissolve or melt in water, and thus can be considered as a permanent hardened body in which a long-term eluviation does not occur.

As discussed above, C12A7 and C3A together form ettringite to achieve the necessary hardening. C12A7 will be discussed in more detail below.

C12A7 reacts rapidly with water and generates a lot of heat, possibly producing hydrate such as $3CaO.Al_2O_3.6H_2O$ and aluminum hydroxide gel. Aluminum hydroxide is more advantageous because it has better acid resistance than calcium hydroxide.

In natural conditions, C12A7 is uncommonly found in Mayenite minerals. Sometimes, it is also present in natural cement. However, as described above, C12A7 may preferably be produced by the low-temperature calcination of Portland cement.

In the presence of calcium hydroxide, the hardening time is rapidly reduced as the content of C12A7 is increased. However, if there is much more C12A7 than C3A in the composition prior to the application thereof, the hardening time may become excessively short and workability may be deteriorated. Thus, the operator may be advised to appropriately adjust the hardening time by adjusting the weight ratio of C12A7 to C3A (or other ratios of a similar nature) when using the composition for a procedure. According to the tests conducted by the inventors, in the composition prior to the application, the content of C12A7 may be equal to or less than 1.5 times that of C3A by weight. Preferably, the content of C12A7 may be equal to or less than that of C3A. More preferably, the content of C12A7 may be 0.5 to 1 times that of C3A. Most preferably, the content of C12A7 may be equal to that of C3A.

Calcium Hydroxide

According to a preferred embodiment of the invention, it may be necessary for the composition of the invention to contain calcium hydroxide for rapid hardening. In general, the effect of facilitating the hardening becomes greater as the specific surface area of the calcium hydroxide is increased. In this regard, it is preferable that the average particle size of the calcium hydroxide is 15 microns or less. It is more preferable that the average particle size is 10 microns or less. It is most preferable that the average particle size is less than 5 microns.

The calcium hydroxide can increase the concentrations of hydration reactants during the initial hydration reaction to increase the rate at which calcium aluminate produces ettringite, thereby reducing the hardening time.

Actually, the calcium hydroxide is a useful material that has long been recognized in tooth preservation. It is also possible to treat dental caries or protect dental pulp exposed due to accidents using only the calcium hydroxide. Overall, maintaining the calcium hydroxide in a stable, insoluble compound can increase the safety and efficacy of procedures.

However, if the amount of the calcium hydroxide is increased more than necessary, the reaction rate becomes excessively fast to cause deterioration in workability, and particularly in strength.

Therefore, it is preferable that the calcium hydroxide is contained in the composition of the invention at 3 to 7% of Portland cement by weight.

Gypsum Component (Mainly Anhydride, Semi-Hydrate, or Dihydrate of Calcium Sulfate)

As described above, a gypsum component is important for the production of ettringite in the present invention. The gypsum component can usually be anhydride, semihydrate, or dihydrate of calcium sulfate. According to one embodiment of the invention, if the gypsum component is eluted from the Portland cement formed through a calcination process, it may be mainly calcium sulfate semi-hydrate (i.e., calcined gypsum). According to a more preferred embodiment of the invention, if the gypsum component is artificially added to the composition of the invention, it may be anhydride or dihydrate of calcium sulfate. In any case, the gypsum component may preferably be contained in the composition of the invention at 15 to 200% of the alumina component by weight. This is because when the weight ratio of the gypsum component to the alumina component is less than 15%, the rate of ettringite production is reduced and the amount of the produced ettringite becomes excessively small, so that the amount of $SO_4^{2-}$ becomes absolutely insufficient and the strength of the hardened body is reduced while the produced ettringite is decomposed into monosulfate. Meanwhile, when the weight ratio of the gypsum component to the alumina component exceeds 200%, the development of strength of the hardened body is delayed due to recrystallization into gypsum dihydrate caused by the excessive gypsum content, or due to the relatively small amount of the alumina component.

Thus, by allowing the gypsum component to be contained in the composition of the invention to such an extent as above, it is possible to effectively produce the ettringite essential to the hardening reaction of the invention. Accordingly, the layer of the ettringite may be formed on the surface of C3A particles so that calcium silicate components (i.e., C3S, C2S, etc.), which are other components in Portland cement, are also hydrated to participate in the hardening (i.e., to cause C—S—H gel to be produced) while the next hydration of C3A is delayed, and the production of monosulfate hydrate or the like, which is unfavorable to the hardening, is maximally inhibited.

Setting Accelerator

According to one embodiment of the invention, a setting accelerator for facilitating hydration reaction may be further contained in the composition of the invention. Lithium carbonate, sodium carbonate, sodium sulfate, magnesium sulfate, aluminum sulfate and the like can be used as the setting accelerator. At least one setting accelerator may be selected from the group consisting of these, and particularly sodium carbonate may be preferred. According to one embodiment of the invention, the content of the setting accelerator is preferably 7 parts by weight or less per 100 parts by weight of C12A7 (when the setting accelerator is sodium carbonate). When the content exceeds 7 parts by weight, the durability of the hardened body is disadvantageously deteriorated.

Pozzolanic Substance

According to one embodiment of the invention, it may be necessary for the composition of the invention to contain a pozzolanic substance. Pozzolanic substances are substances that can react with calcium hydroxide to cause a known pozzolanic reaction. (For example, there may be natural pozzolanic substances from volcanic ash, tuff, silicate clay, diatomite and the like, or artificial pozzolanic substances from fly ash, calcined clay, silica gel, silica fume and the like.)

The pozzolanic reaction will be discussed in detail below. First, the mechanism of the pozzolanic reaction will be briefly discussed. A component such as $SiO_2$ and $Al_2O_3$ eluted from a pozzolanic substance reacts slowly with calcium hydroxide, which is produced when C3S, C2S or the like constituting Portland cement is hydrated, to produce insoluble calcium silicate hydrate (i.e., C—S—H gel) or calcium aluminate hydrate (i.e., C-A-H gel). This causes the structure of the hardened body to be denser.

The pozzolanic reaction can contribute to suppression of heat generation due to quick setting of calcium aluminate in the composition of the invention, which is particularly characterized by having a short hardening time. In addition, insoluble hardened microbodies produced by the pozzolanic reaction increase the long-term strength of the hardened body formed by the composition of the invention, and substantially fill the pores of the hardened body to enhance its hermeticity, thereby contributing to suppression of bacterial penetration or the like. Further, it is particularly suitable to an oral environment due to its excellent chemical resistance, salt resistance and the like.

Various pozzolanic substances can be employed as discussed above, and some notable ones are further discussed below. The following ones may be redundantly employed.

(1) Volcanic Glass (Obsidian)

Volcanic glass containing silica, alumina and the like is glass made from magma ejected by volcanic eruption and rapidly cooled in the atmosphere to have an amorphous and porous structure with a large surface area. This structure causes the volcanic glass to have high pozzolanic reactivity.

(2) Clayish Pozzolanic Substance

While the volcanic glass can be used without additional heat treatment for enhancing the pozzolanic properties, clayish pozzolanic substances are poorly hardened due to poor pozzolanic reactivity unless the crystal structure of the clay minerals is destroyed by heat treatment. Accordingly, the clayish pozzolanic substances may be calcined at a temperature of about 600 to 900° C. to form an amorphous structure, or an irregularly formed silica or alumina structure may be used. This may also be referred to as calcined clay.

(3) Siliceous Pozzolanic Substance

Silica fume is a representative of siliceous pozzolanic substances. It is composed of about 30% or more of spherical particles, and the size of the particles are mostly less than 1 micron and the average thereof is about 0.1 micron. It consists of 90% or more of amorphous silica. The fineness value thereof is very high and the amount of silica is large, resulting in a very effective pozzolanic reaction.

(4) Nano $Al_2O_3$ Particles and Nano $SiO_2$ Particles

The reason for adding nano $Al_2O_3$ particles (i.e., nano-alumina particles) is to form C-A-H gel. To this end, amorphous or glassy alumina may be used. The alumina enhances pozzolanic reactivity. In order to improve the physical properties of the composition of the invention, it is possible to use nano $Al_2O_3$ having a high purity of 99.9% and a high Blaine fineness value (e.g., 60 $m^2/g$). It may be added to the composition of the invention until the weight ratio of about 2% is reached. Although a substantial strength enhancement effect is achieved even when it is added until the weight ratio of about 1% is reached, workability is disadvantageously deteriorated when the weight ratio exceeds 2%.

Nano $SiO_2$ (i.e., nano-silica) is a more powerful pozzolanic substance than silica fume, and a sufficient effect can be achieved even with a small amount of 3% or less by weight of the composition. Obviously, the smaller the particle size of the substance, the more pronounced the strength enhancement effect.

Meanwhile, an appropriate amount of a known radiopaque substance may be added to the composition of the invention depending on the specific use, as decided by those skilled in the art.

In the following, conducting a test will be described in which the compositions of the invention are prepared by various methods and then the hardening times of the prepared compositions are compared.

The inventors prepared hydraulic binder compositions using the following components or compositions.

Case 0: white Portland cement only
Case 1: 9 parts by weight of white Portland cement, 1 part by weight of C12A7, and 0.5 parts by weight of calcium hydroxide
Case 2: 9.5 parts by weight of white Portland cement, 0.5 parts by weight of C12A7, and 0.5 parts by weight of calcium hydroxide
Case 3: 36 parts by weight of white Portland cement, 4 parts by weight of C12A7, 1 part by weight of calcium hydroxide, and 2 parts by weight of calcium sulfate (0.5 part by weight of gypsum)

As a result of the test conducted with the prepared compositions, the hardening times of the compositions of Cases 0 to 3 were 4 hours, 2 minutes, 3 minutes, and 5 minutes, respectively.

In the following, conducting another test will be described in which the compositions of the invention are prepared by various methods and then the biocompatibility of the prepared compositions is compared.

In this test, the biocompatibility of the hydraulic binder compositions of Cases 0 to 3 was checked by observing the activity of alkaline phosphatase and the degree of mineralization-related gene expression. Meanwhile, in order to obtain a control group, the biocompatibility of the case (CON) without any treatment was checked together. Further, for comparison with the prior art, the biocompatibility of the case (PR) using ProRoot MTA (by Dentsply in Tulsa, Okla., USA), which is a well-known conventional composition, was checked together.

(1) Activity of Alkaline Phosphatase

Each of the compositions of Cases 0 to 3 and Cases CON and PR was mixed with distilled water, and then placed in a 1 mm×5 mm mold and hardened. After each sample was stored in 10 ml of MEM-α for 3 days, a material extract was obtained. $2 \times 10^4$ immortalized human dental pulp cells were dispensed into a 24-well culture plate and then cultured at a temperature of 37° C. and 5% of carbon dioxide. After a 1-day cell attachment period was given, the above material extract was substituted and then further cultured for 1 day, 3 days, and 7 days. After each culture was finished, alkaline phosphatase activity was measured and statistical analysis was performed using one-way dispersion analysis and Tukey's test ($p=0.05$). Referring to FIG. 1, which is a graph of the result, the compositions according to the invention (i.e., those of Cases 1 to 3) show superior or comparable biocompatibility (i.e., the same or lower alkaline phosphatase activity) as compared with those of Cases CON, PR and 0.

(2) Degree of Mineralization-Related Gene Expression

Figure 2:
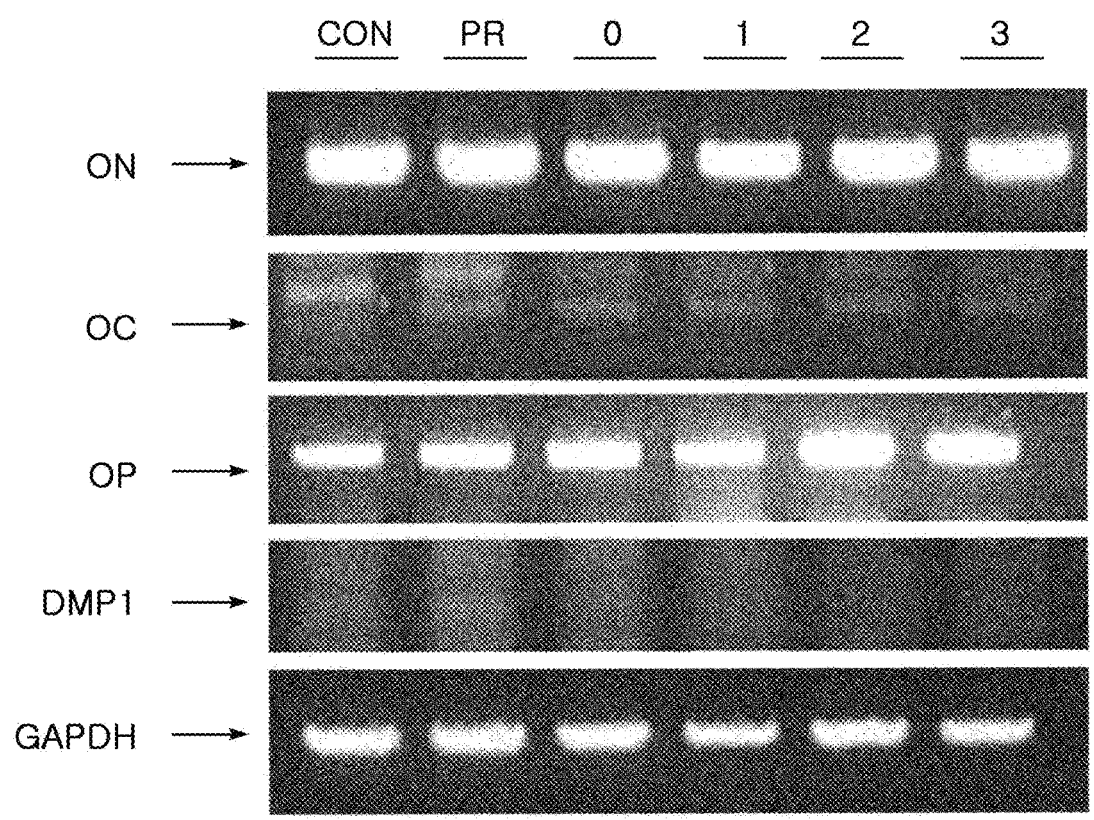
FIG. 2 is a result image obtained from a test conducted according to one embodiment of the invention.

Each of the compositions of Cases 0 to 3 and Cases CON and PR was mixed with distilled water, and then placed in a 1 mm×5 mm mold and hardened. After each sample was stored in 10 ml of MEM-α for 3 days, a material extract was obtained. $2 \times 10^4$ immortalized human dental pulp cells were dispensed into a 24-well culture plate and then cultured at a temperature of 37° C. and 5% of carbon dioxide. After a 1-day cell attachment period was given, the above material extract was substituted and then further cultured for 1 day, 3 days, and 7 days. After each culture was finished, the degrees of expression of mineralization-related genes (i.e., ON, OC, OP, DMP-1 and GAPDH) were examined using real-time PCR. FIG. 2 is an image showing the result. According to the result, no differences in the degrees of expression of the mineralization-related genes were observed despite the differences of the material extracts.

What is claimed is:

1. A rapid-setting hydraulic binder composition, comprising:
   Portland cement calcined at a low temperature of 800° C. to 1,250° C.; and
   calcium hydroxide,
   wherein the Portland cement comprises tricalcium aluminate (C3A) and dodecacalcium heptaaluminate (C12A7),
   wherein content of the C12A7 is equal to or less than 1.5 times that of the C3A by weight, and
   wherein an average particle size of the calcium hydroxide is 15 micron or less, and the calcium hydroxide is contained at 3 to 7% of the Portland cement by weight.

2. A rapid-setting hydraulic binder composition as claimed in claim 1, further comprising anhydride or hydrate of calcium sulfate.

3. A rapid-setting hydraulic binder composition as claimed in claim 2, wherein the hydrate of the calcium sulfate is calcium sulfate hemihydrate or calcium sulfate dihydrate.

4. A rapid-setting hydraulic binder composition as claimed in claim 1, further comprising calcium sulfate hemihydrate eluted from the Portland cement.

5. A rapid-setting hydraulic binder composition as claimed in claim 1, further comprising a pozzolanic substance.

6. A rapid-setting hydraulic binder composition as claimed in claim 5, wherein the pozzolanic substance includes at least one of volcanic glass, a clayish pozzolanic substance, a siliceous pozzolanic substance, nano-alumina particles, and nano-silica particles.

7. A rapid-setting hydraulic binder composition as claimed in claim 6, wherein the pozzolanic substance is nano-alumina particles, which are contained at 2% or less by weight.

8. A rapid-setting hydraulic binder composition as claimed in claim 6, wherein the pozzolanic substance is nano-silica particles, which are contained at 3% or less by weight.

9. A rapid-setting hydraulic binder composition as claimed in claim 1, further comprising at least one setting accelerator selected from a group consisting of lithium carbonate, sodium carbonate, sodium sulfate, magnesium sulfate, and aluminum sulfate.

10. A rapid-setting hydraulic binder composition as claimed in claim 9, wherein the setting accelerator is sodium carbonate and contained at 7 parts by weight or less per 100 parts by weight of the C12A7.

* * * * *